United States Patent [19]

Enloe et al.

[11] Patent Number: 4,666,647
[45] Date of Patent: May 19, 1987

[54] APPARATUS AND PROCESS FOR FORMING A LAID FIBROUS WEB

[75] Inventors: Kenneth M. Enloe, Neenah; Timothy L. Wehman, Menasha, both of Wis.

[73] Assignee: Kimberly-Clark Corporation, Neenah, Wis.

[21] Appl. No.: 807,381

[22] Filed: Dec. 10, 1985

[51] Int. Cl.<sup>4</sup> ............................................. B27N 3/04
[52] U.S. Cl. ...................................... 264/121; 19/148; 19/308; 264/118; 264/120; 264/517; 425/80.1; 425/83.1
[58] Field of Search ................ 425/80.1, 81.1, 82.1, 425/83.1; 264/109, 116, 118, 121, 517, 518, 120; 156/62.2, 62.4; 19/148, 308

[56] References Cited

U.S. PATENT DOCUMENTS

| | | | |
|---|---|---|---|
| 2,635,301 | 4/1953 | Schubert et al. | 425/83.1 |
| 3,256,569 | 6/1966 | Draving | 19/308 X |
| 3,501,813 | 3/1970 | Lee et al. | 19/301 |
| 3,518,726 | 7/1970 | Banks | 28/102 |
| 3,575,472 | 4/1971 | Brewster et al. | 19/308 X |
| 3,598,680 | 8/1971 | Lee | 156/62.2 X |
| 3,682,761 | 8/1972 | Lee et al. | 428/171 |
| 3,757,785 | 9/1973 | Wosaba, II | 604/374 |
| 3,766,922 | 10/1973 | Krusko | 604/374 |
| 3,848,598 | 11/1974 | Mesek | 604/374 |
| 3,860,002 | 1/1975 | Kolbach | 604/365 |
| 3,924,626 | 12/1975 | Lee et al. | 604/366 |
| 3,939,240 | 2/1976 | Savich | 264/109 X |
| 3,961,397 | 6/1976 | Neuenschwander | 425/82.1 X |
| 3,962,753 | 6/1976 | Dunn | 264/121 X |
| 3,973,291 | 8/1976 | Kolbach | 19/148 |
| 3,975,222 | 8/1976 | Mesek | 156/62.2 |
| 3,994,047 | 11/1976 | Lee et al. | 28/104 |
| 4,005,957 | 2/1977 | Savich | 264/112 X |
| 4,016,628 | 4/1977 | Kolbach | 19/148 |
| 4,103,058 | 6/1978 | Humlicek | 428/171 |
| 4,223,677 | 9/1980 | Anderson | 604/365 |
| 4,382,758 | 5/1983 | Nopper et al. | 425/82.1 |
| 4,388,056 | 6/1983 | Lee et al. | 425/83.1 |
| 4,592,708 | 6/1986 | Feist et al. | 19/148 X |

Primary Examiner—Richard L. Chiesa
Attorney, Agent, or Firm—Paul Yee

[57] ABSTRACT

Apparatus and process for forming a laid fibrous article includes a foraminous forming surface for depositing thereon of fibers under the influence of a pressure differential imposed on the surface, wherein the improvement comprises the provision of a concavely contoured portion of the forming surface to yield a non-stepwise gradation in basis weight of the laid fibrous article. The concavely contoured surface portion is bounded by walls defining angles of from about 45° to 68°, whereby the laid fibrous article is readily removable from the forming surface, which may comprise the cylindrical surface of a rotating drum.

27 Claims, 10 Drawing Figures

APPARATUS AND PROCESS FOR FORMING A LAID FIBROUS WEB

BACKGROUND OF THE INVENTION

1. Field of the Invention

This invention generally relates to apparatus and method for forming a laid fibrous article, characterized by a non-stepwise gradation in basis weight across its surface, such as is useful as an absorbent pad for applications such as disposable diapers, sanitary napkins, and the like.

2. Description of the Prior Art

In the general practice of forming fibrous web materials as laid fibrous articles, it has been common practice to utilize a fibrous sheet of cellulosic or other suitable fibers which is fiberized in a conventional fiberizer or other shearing device to form discrete fibers, which then are entrained in an air stream and directed to a foraminous forming surface whereon the fibers are deposited to form a pad of fluff, i.e., a nonwoven mat of randomly arrayed fibers containing substantial interstitial void space and being highly compressible in character.

The forming surface utilized in such systems typically is constructed as a wire or screen grid and typically employs pneumatic flow means, such as vacuum suction apparatus, to define a differential pressure zone on the forming surface and impose a pressure differential thereon, whereby the air in the air-entrained fiber stream is passed through the openings or perforations in the screen or grid of the forming surface. The use of vacuum suction to draw the air-entrained fibers stream of the forming surface, with passage of the air component through the forming surface, is highly efficient and lends itself to high-speed commercial operations.

Nonetheless, the use of such "vacuum deposition" systems for forming air-laid fibrous articles has the corresponding disadvantage that it is frequently difficult to quickly remove the laid fibrous article from the forming surface. This difficulty arises because formation of fibrous webs formed by vacuum-suctioned deposition of the fibers onto the forming screen produces a highly mechanically interlocked array of fibers, due to the many cross-over points of contact on a given single fiber relative to other fibers deposited therewith. Such interlocking produces a desirable structural integrity for the fibrous material, but the varied cohesive character of the fibrous mat hinders its removal when the entire web is attempted to be removed from the forming surface. This problem of removability is further exacerbated by the fact that the screen and grid elements commonly employed for constructing such forming surfaces become filled with the mechanically interlocked fibers around the strands or wires of the surface itself which increases the adhesion of the fibrous web to the forming surface.

Additionally, when a negative pressure, viz, vacuum suction is applied to the forming surface, the same must be terminated or otherwise overcome to break the vacuum force retaining the fibrous web on the forming surface. Therefore, in order to overcome the problem of removing laid fibrous webs deposited by vacuum suction on forming surfaces, it has been conventional practice to employ a pressurized stream of air, either as a side stream of the gas flow passing through the forming surface or as a separate gas stream, to break the vacuum imposed in the forming step upstream of the removal step and thereby forcibly remove the laid fibrous web from the forming screen or grid, typically onto a take-off conveyor or other similar means.

In the prior practice of forming laid fibrous articles, various means have been proposed in the art for providing the fibrous article with gradations in basis weight across the surface thereof. Such gradations can, for example, enhance the efficiency of the fibrous article in end usages, such as disposable diapers and sanitary napkins. Various means thus have been proposed for producing longitudinal gradations of basis weight, i.e., in the machine direction, and for providing transverse basis weight variations, i.e., in the cross-machine direction. In many instances, however, the aforementioned removability problem is rendered more severe by the fact that the additional basis weight imparted to the article provides more resistance to removal by a gas nozzle or other imposition of a pressurized gas stream. Accordingly, it would be a substantial advance in the art to provide means and method for forming a laid fibrous article characterized by a gradation in basis weight across the surface of the article, but which is readily removable from the forming surface subsequent to the laying of the article thereon.

U.S. Pat. No. 4,388,056 to Lee et al. discloses an apparatus for continuously forming an air-laid fibrous web, comprising a laydown drum having a circumferentially segmented annular-shaped plenum comprising a multiplicity of circumferentially spaced transverse plenum segments, and a partially masked foraminous laydown surface having oppositely contoured, cyclically undulating side edges defining cyclically circumferentially spaced relatively wide masked and relatively narrow masked transverse areas of the surface, which together define the radially outward facing boundary of the plenum. Constant differential pressure means are employed for drawing air through the foraminous laydown surface and the plenum from an air-entrained-fiber deposition chute as the drum is rotated. The specific improvement of the invention comprises stationary adjustable air flow modulating means (shutter plates) disposed adjacent the radially inwardly disposed boundary of an arcuate portion of the plenum circumferentially spanning a plurality of the transverse plenum segments. In such manner, the pressure across the relatively widely masked transverse sections of the laydown surface can be adjusted without substantially affecting the pressure across the relatively narrow masked transverse sections of the laydown surface.

This apparatus purportedly permits the formation of a fibrous web severable into uniform, contoured articles, such as fibrous absorbent cores for disposable diapers, having relatively thick narrow and adsorbent crotch areas, and relatively thin waistband regions, without stepwise basis weight gradients. Thus, the areas of the foraminous laydown surface (screen) having the largest pressure differential across them (i.e., the narrow areas) experience greater fiber buildups or accumulations than the areas of the screen having lower pressure differentials across them (i.e., the wide areas), the narrow areas corresponding to the crotch regions of the web articles and the large areas corresponding to the waistband regions thereof.

Although the apparatus disclosed in the —056 patent is alleged to provide a smooth basis weight gradation in the machine direction (i.e., longitudinally) in the fibrous articles formed thereon, as noted particularly with reference to FIGS. 7 and 8 of this patent, the basis weight gradation of the fibrous article is both longitudinally and laterally symmetrical in distribution. Accordingly, the greatest basis weight occurs in a circular shaped region centered at the crotch with the basis weight uniformly radially decreasing therefrom, such that lines of nominally equal basis weights describe concentric circles radiating outwardly from such central region of highest basis weight. This design provides a high basis weight in the frontal crotch region where same is usefully employed. However, for reasons of liquid retention, it is more advantageous to provide a longitudinally extending central region of high basis weight relative to the longitudinal peripheral margins, and further to provide a higher basis weight in the front panel of the fibrous article relative to its rear panel (the front and rear panels being considered here as the demarcated opposed symmetrical portions produced when the fibrous article is folded along a lateral fold line midway along its longitudinal extent). In comparison to these optimal basis weight characteristics of the fibrous web article, the fibrous articles produced by the apparatus of the Lee, et al. patent are seen to be deficient, particularly in the steady decline of such article's basis weight along the full longitudinal dimension of the front and rear panels, from a point centered at the crotch region of the article.

U.S. Pat. No. 3,939,240 to P. P. Savich discloses a method of dry forming fibrous pads by means of a condenser roll having three-dimensional cavities circumferentially disposed about the periphery thereof. The cavities each have foraminous bottom and side surfaces, with the surface area of the cavity being greater than the surface area of the opening into the cavity. Vacuum is applied through the foraminous surfaces of each cavity to pull the air component of a fibers/air suspension through the foraminous surfaces, thereby depositing the fibers carried in the air suspension onto the cavity surfaces. A transfer conveyor is proximately disposed to the cavity opening at its discharge position and vacuum also is supplied through the transfer conveyor, to transfer the fibrous layer from the cavity onto the conveyor. The fibers deposited on the transfer conveyor are confined to an area substantially equal to the surface area of the cavity opening, so that the fibers are consolidated as they are transferred from the cavity onto the conveyor, forming fibrous pads having a greater basis weight than the basis weight of the fibrous layers formed in the cavities. This patent, in addition to embodiments disclosing the formation of discrete fibrous pads unassociated with any fibrous web, discloses an embodiment in which the outer periphery of the forming roll surrounding each cavity is also foraminous. In such manner, the fibrous pads formed from the fibrous layers within each cavity will be integrally joined with fibrous web sections of a lower basis weight.

U.S. Pat. No. 4,223,677 to J. E. Anderson discloses an absorbent fibrous structure which includes intermingled absorbent fibers of a varying length up to about 6.35 millimeters. The fibers are disposed in different classified layers having differing weighted average fiber length in each of the layers, with the weighted average fiber length decreasing from layer to layer in a direction from one outer surface to the opposite outer surface. The separate layers of the absorbent pad are not disclosed as having any varying weight within the respective layers, so that the basis weight therefore is constant along the longitudinal and transverse dimensions of the pad.

An apparatus for forming fibrous pads is disclosed in U.S. Pat. No. 3,973,291 to C. G. Kolbach, comprising a pad assembly having spaced three-dimensional pad-receiving compartments, separated by air-impermeable regions. The pad-receiving compartments are defined by lower air-permeable surfaces and air-impermeable side walls extending outwardly therefrom. The side wall sections of each compartment are movable relative to the lower air-permeable surface to assist in releasing formed pads from the compartments.

In column 8, lines 41 et seq, it is alleged that the patentee has discovered that formation of a profiled fibrous pad, i.e., one with a varying basis weight, "cannot be controlled within close tolerances by establishing a different amount of open area through which air can be drawn by a vacuum box through different predetermined regions underlying the different predetermined sections of the pad-receiving compartment in which different weights of fibers per unit area are to be deposited". Based on this discovery, it is contended that "the only effective means for establishing different weights of fiber per unit area in different predetermined regions of a fibrous pad, while maintaining close tolerances, is to completely form each predetermined region with a specific weight of fibers per unit area therein substantially independently of the formation of every other predetermined region having a different weight of fibers per unit area therein". The disclosed method thus involves completely masking off a source of vacuum to all sections of each pad-receiving compartment except the section in which region a fibrous pad having a particular weight of fibers per unit area is to be formed. After this region has been completely formed, the vacuum source underlying the formed region is completely masked to the passage of air, and a second section of each pad-receiving compartment is exposed to vacuum to form a predetermined region on the pad having a different weight of fibers per unit area therein. Thus, the patentee discloses a serial masking-unmasking sequence to provide the finished article.

U.S. Pat. No. 3,501,813 to C. A. Lee, et al. discloses a method and apparatus for forming a single integral web of air-laid fibrous material with non-uniform cross-sectional thickness. The disclosed apparatus employs a carrier moving at uniform rate whereon first and second quantities per unit time of loose fibrous material are conveyed by air and deposited on first and second different portions of the carrier. The uneven distribution of material on the foraminous carrier is achieved by providing the air stream with a velocity profile in which certain portions have a higher velocity than the adjoining portions and convey a greater amount of material to associated portions of the carrier, by creating a greater vacuum or suction behind the associated portions of the foraminous carrier than behind adjacent portions so as to draw the air through the screen at the same rate as it arrives at the screen. This in turn is achieved by shielding a portion of the carrier from the air stream while deflecting the air stream toward the unshielded portion.

As shown in FIG. 5 of the -813, Lee, et al. patent, baffles 46 are provided to constrict the conduit through which air is delivered to the carrier, with valves 48 being provided to permit the establishment of a lower pressure behind certain portions of the carrier than behind adjacent portions. The baffles and valves are both selectively operable to provide the web with a predetermined profile or cross-sectional configuration. The web produced by such apparatus, as disclosed in column 4, lines 1-3, has a raised or thick center portion flanked by substantially thinner edge portions. Thus, baffles are provided upstream of the forming surface and valves downstream from the forming surface, with respect to the path of the air flow therethrough. Each of the baffles is in the form of a flat plate beveled at its innermost end and positioned in a slot defined by flanges, which by virtue of the inclination of the flanges, cause the baffles to extend inwardly from opposite sides of the central conduit and be inclined in the direction of flow of the air stream. Accordingly, the baffles constrict the conduit within the delivery duct to narrow the air stream to a centrally disposed vertically oriented flow and thereby increase velocity of the air stream in the central area of the conduit.

The foraminous carrier is supported by a vacuum box which also serves to control the passage of air through the carrier. The vacuum box includes a grid plate provided with a plurality of openings which affords communication between the vacuum chamber and the surface of the grid plate, thereby creating a section which removes air arriving at the surface of the plate. Each opening in the grid plate has associated therewith a valve which permits selective control of air pressure at each opening and consequently, permits variations in the degree of suction across the grid. The web formed on the carrier screen is removed therefrom by a take-off roll associated with nozzles proximate thereto which direct jets of air outwardly through the carrier screen thereby assisting in the separation of the web from the screen, and cleaning the screen of adhering fibrous particles.

U.S. Pat. No. 3,598,680 to C. A. Lee discloses a tandem air former for forming a fibrous web of non-uniform cross-sectional thickness, by air-laying fibrous material at a first station and then air-laying additional fibrous material at a second station downstream from the first to overlap at least partially the fibrous material deposited at the first station. A pressure differential is maintained across the web during formation, to cause air to flow through the thicker portion of the web as well as the thinner portions at substantially the same rate as it approaches the web. The air flow passageway to the foraminous carrier is defined in part by deckle plates which are adjustable transversely of the web being formed, i.e., the respective opposed deckle plates may be shifted toward or away from one another to vary the width of the air stream passing between them and, in consequence, the width of the pad being deposited on the web.

U.S. Pat. No. 3,975,222 to F. K. Mesek discloses a disposable diaper assembly comprising an absorbent fibrous panel which is double contoured, being centrally contoured in the transverse and longitudinal directions to produce a smooth peak on one major surface. Two rolls of compacted wood are provided to feed a source of short cellulosic fibers to a grinding mill from which a stream of fibers is blown downwardly through a duct onto a belt as a layer. The patent discloses that the duct may be baffled to allow more fibers to be concentrated at the central portion of the web. Another method comprises grinding fibers at one station and depositing them to produce a continuous web at the maximum width desired and grinding fibers at another station and depositing them downstream along a band of lesser width on top of and along the median of the first continuous web. A longitudinal contour of the fibrous web is achieved by varying the speed at which fibers are deposited on the belt, so that by decreasing the deposition rate the marginal areas of reduced thickness are produced and correspondingly, by increasing the deposition rate, the thickened central contour portion is produced. The contour thickness is preferably formed to provide a ratio of apex thickness to corner thickness in the range of 1.5 to 4.

U.S. Pat. No. 3,994,047 to C. A. Lee, et al. discloses apparatus for making two-layer composite pads formed simultaneously on a twin wire arrangement, with the units of one layer being of hourglass and the other, ovate in shape. The layers are formed on respective foraminous carriers in a forming chamber. In the disclosed system, it is necessary to keep the respective forming screens in register with one another inasmuch as the webs formed thereon are subsequently joined to form the aforementioned composite. For such purpose, the respective forming screens have registration indicia which may be sensed as for example by an electric eye, to indicate any misregistration whereby the appropriate tension roll for the respective forming screen is adjusted to maintain registration. In order to drive air through the laydown fibrous web layers at the same rate at different portions of the forming path, the pressure differential and the respective forming layers increase in the direction of travel of the carrier screens, by separately controlled air flow through suction boxes associated therewith. Each of the suction boxes includes a damper for controlling the rate of flow of air through each of the boxes. The forming chamber also has a perforated wall opening through which additional air may be admitted to the forming chamber.

A removal means is provided at the exit end of the forming chamber to remove any excess fibers as deposited on the respective carriers. This removal means includes a snout 110 which in turn includes a septum and walls defining openings through which air is sucked by a blower at relatively high velocity. The walls of the snout are disposed relatively close to the tops of formed layers of fibers to provide a rush of air over the exposed surfaces thereof. This shears fibers from the surfaces of the layers and entrains the fibers in the air stream removed therefrom. The foraminous carrier screens in this system include open areas on which the respective fibrous web components are formed, the areas outside of such patterned open areas being impervious (impermeable) to air flow.

U.S. Pat. No. 4,016,628 to C. G. Kolbach discloses an apparatus for forming a fibrous web which includes a medial portion integrally joined through the randomly arranged fibers thereof to flanking side portions and flanking end portions, the medial portion having a greater basis weight and thickness than the respective flanking side and end portions. The patent discloses at column 3, lines 29-40 that the higher basis weight medial portion of the fibrous web can be substantially uniform in basis weight or can be profiled, e.g., with the center section of the medial portion being provided with a greater basis weight of fibers than the flanking end sections (for use as disposable diapers for girls, and alternatively a forward section of the medial portion being provided with a greater basis weight of fibers therein than a rearward section thereof, as when the fibrous web is used as a disposable diaper for boys). In addition, it is disclosed at column 3, lines 41-47 that the specific shape of the medial portion can be varied within wide limits, such as being substantially rectangular or contoured to include a reduced width crotch region which provides a more conformable structure in the perineal region of a wearer.

Embodiments of the product fiber web are shown in FIGS. 11-16 of the Kolbach patent, wherein the medial portion of the web is profiled to itself to have different basis weights in different predetermined sections thereof, such as the medial portion having a center section of greater basis weight than the adjoining end sections of the medial portion (FIGS. 11, 13 and 15) and a configuration wherein a greater basis weight section of the medial portion is provided on the forward half thereof (FIGS. 12 and 16).

The disclosed apparatus employs a foraminous forming surface and at least one vacuum box under a discrete section of the forming surface. The foraminous forming surface and the vacuum box are moved in registration with each other through a web forming area so that the same region of the foraminous forming surface is always in overlying relationship to the vacuum box. In operation, an air suspension of fibers is directed onto the surface of a condenser roll assembly, having a foraminous forming surface disposed thereon with circumferentially spaced, three-dimensional compartments therein. Downstream therefrom may be disposed embossing rolls having corresponding surface recesses therein for embossing the fibrous web, to provide surface contours thereon which channel liquids so that the full absorbent capability of the fibrous web is utilized.

The condenser roll assembly includes an air-pervious condenser roll including a perforated cylindrical metal shell and a porous screen secured about the periphery of the shell. The three-dimensional compartments are established by providing discrete cutout regions in the porous screen and cylindrical metal shell and securing a foraminous member to the lower surface of the shell to bridge each cutout region and thereby form the bottom wall of the three-dimensional compartment. In this manner, the porous screen outside the three-dimensional compartments and the foraminous member constituting the lower surface thereof together provide a forming surface for the condenser roll. A vacuum box assembly is mounted within the condenser roll secured to a driving axle so as to be concurrently rotated with the cylindrical shell. The vacuum box assembly includes a plurality of circumferentially spaced vacuum boxes attached to a cylindrical hub, with the outer edges of the sidewalls of the vacuum boxes defining an opening into the vacuum box of the same shape as the three-dimensional compartments, when aligned therewith. Since the cylindrical shell and the vacuum box assembly are concurrently rotated at the same angular velocity, each vacuum box will underlie its respective compartment throughout the entire path of rotation. Removal of the formed web from the condenser roll is effected by terminating the partial vacuum through the forming surface; this is achieved by a masking member circumferentially extending in coaxial manner with the condensing roll and the vacuum box assembly, and interposed therebetween. The masking member is perforated over a portion of its length and is imperforate on the lower section.

Accordingly, the condenser roll and vacuum box assembly during its travel will encounter the imperforate portion of the masking member, thereby blocking the vacuum imparted to the formed web, so that the web may be removed by a take-off conveyor to which vacuum is applied. The masking member is not rotated, so that the condenser roll and vacuum box assembly pass circumferentially adjacent to the masking member over its full circumferential extent. Vacuum is provided to the forming surface by suction through an annular passage in flow communication with the vacuum boxes. The portions of the interior of the condenser roll are in flow communication with a second annular passage with a reduced vacuum level being imposed thereon. The patent states at column 12, lines 56-62 that since the entire forming surface of the condenser roll is exposed to vacuum for the same period of time, a greater effective or total volumetric air flow will be established through the bottom walls of the three-dimensional compartments, which are subject to a greater partial vacuum than the surfaces flanking the three-dimensional compartments. This greater effective volumetric air flow results in the deposition of a greater weight of fibers in each of the three-dimensional compartments than on the foraminous surface regions surrounding the three-dimensional compartments. The drawings of this apparatus, such as FIG. 3, indicate the three-dimensional compartment to be relatively shallow and to be bounded by radially extending wall surfaces which appear to be perpendicular to the forming surface.

In a modified embodiment of the invention, as shown in FIGS. 17-19 of the patent, a masking member is employed in which the imperforate circumferential portion has at one end thereof "finger portions" which underlie the three-dimensional compartments at their extremities; these finger portions are followed circumferentially by a central blocking portion of the mask member which in turn underlies the central portion of the three-dimensional compartment when same is passed over the masking member. The circumferential extent of the finger portions is greater than the circumferential extent of the central blocking portion of the masking member, whereby the central region of the three-dimensional compartment will be exposed for a greater period of time to the vacuum, to achieve formation of thickened central portions of the three-dimensional compartments.

Finally, the patent states at column 15, lines 2-7 that "it is within the scope of this invention to provide a fluid impervious coating directly on the forming surface of the condenser roll in the form of a transverse stripe disposed intermediate adjacent three-dimensional compartments to achieve direct formation of discrete fibrous webs on the forming surface". It is apparent that this coating serves as a fiber deposition blocking means to segment the web during laydown, in discrete segments.

U.S. Pat. No. 3,518,726 to C. T. Banks discloses apparatus for making sanitary napkins from fluff derived from wood pulp which has been disintegrated. A forming drum is employed which has on its cylindrical surface a series of planar chord-like plate members which are perforated, each plate having perforations more closely spaced relative to one another in the central portion of the plate as compared to the end segments of the chord-like plates, wherein the perforations are more distantly spaced relative to one another. The forming drum is in gas flow communication with vacuum suction means, whereby areas of fluff deposited on the drum compartments are of greater thickness at their centers relative to their ends, due to the arcuate shape of the side plates defining each compartments on the drum periphery. In addition, more fluff collects in the central regions of the cavities than in the end regions due to the fact that the spacing between holes is less in the central regions than in the end regions, so that the resulting pad is thicker in its central region.

This patent also discloses an embodiment wherein a compressed, high-density segment is provided for embedment in one of the flat faces of the pad. In this embodiment, a second assembly takes disintegrated pulp fibers and collects some on a forming drum which is composed of a cylinder of perforated sheet material, with a vacuum box in communication with a central opening through the rotatable drum for maintaining vacuum therein. An end closure plate portion extends across and within the forming drum, being sealed with respect to the inner surface thereof. In this fashion, only about one-half of the forming drum has suction applied to it. This forming drum is in close-spaced relationship to a similar forming drum, whereby each collects fluff on its exterior surfaces for discharge therefrom between the drums in the form of a continuous batt. The batt then is debulked between compression rolls and indented at spaced intervals, following which the batt passes through an embossing assembly which provides a pattern of pyramidal-shaped depressions therein. The batt then is cut into segments and transmitted by conveyor means to the first-mentioned forming drum, on which the high-density segment is centrally disposed on the forming cavity and overlaid with fluff. The resulting pads,, containing the high-density segments on their lower faces, are cut in a cutter assembly and passed to a wrapping means whereon a gauze web is folded around the individual pads, pleated and severed to form the individual sanitary napkin.

As is apparent from the foregoing, the prior art has proposed a great variety of systems for producing variant basis weight articles by air-laying of fibers, and has proposed numerous means of removing the laid fibrous article from the forming surface, yet all are characterizable to some degree by deficiencies in terms of the mechanical complexity involved as well as in deficiencies of the absorbent material which is produced.

Insofar as the latter point, i.e., the character of the absorbing material produced by laying of the fibrous material, is concerned, it is highly desirable in applications such as the production of absorbent pads for disposable diapers to provide a non-stepwise gradation of basis weight, with the highest basis weight being provided forward of the lateral center line (crotch fold line) of the article, as compared to the rear portion thereof and to provide in the central region along the length of the article a higher basis weight than the peripheral or marginal areas, and further to provide a still higher basis weight in the central frontal region of the article.

SUMMARY OF THE INVENTION

The present invention provides a method and apparatus for forming a laid fibrous article. Generally stated, the apparatus includes a foraminous forming surface for deposit of fibers under the influence of a pressure differential imposed on the surface. The forming surface includes one or more concavely contoured portions of the forming surface for providing a non-stepwise gradation in basis weight of the laid fibrous article. The concavely contoured surface portion is bounded by walls angularly oriented with respect to the plane of the forming surface proximally adjacent the concavely contoured surface portion. This orientation defines an included angle therebetween of not more than 70° and preferably ranging from about 45° to 68°, whereby the laid fibrous article is readily removable from the forming surface.

In one aspect of the invention, the concavely contoured surface portion is elongate in shape, and its bounding walls comprise longitudinal side walls and transverse end walls joined at their bottom edges to a base wall member. In another aspect, the included angles of the longitudinal side walls are between about 55° and 68°; and the included angles of the transverse end walls are between about 45° and 60°.

In another aspect of the invention, the apparatus further comprises a rotatable cylindrical drum whose outer circumferentially extending cylindrical wall surface comprises the forming surface, with a plurality of concavely contoured forming surface portions circumferentially spaced apart thereon, a plurality of radially extending, stationary, baffle wall members sealingly disposed in the interior of said rotatable cylindrical drum to divide the interior into a plurality of arcuate, stationary segments defining and communicating with respective differential pressure zones located on the forming surface. The differential pressure zones comprise a vacuum laydown zone. A pneumatic flow means, comprising vacuum suction means joined in gas flow communication with a first arcuate segment in said rotatable cylindrical drum to define a vacuum laydown zone on the forming surface, draws air through the vacuum laydown zone on the forming surface into the first arcuate segment and out of the rotatable cylindrical drum.

In a process aspect, the invention relates to a method for forming a laid fibrous article, including the steps of providing a foraminous forming surface for deposit of fibers, and imposing a pressure differential on the forming surface, wherein the improvement comprises providing a concavely contoured portion in the forming surface to yield a nonstepwise gradation in basis weight of the laid fibrous article, wherein the concavely contoured surface portion is bounded by walls angularly oriented with respect to the plane of the forming surface proximally adjacent the concavely contoured surface portion, to define an included angle therebetween of not more than about 70°, whereby the laid fibrous article is readily removable from the forming surface.

Other method aspects of the invention include carrying out the method on apparatus in accordance with the invention as described above and in the description of preferred embodiments of the invention.

Generally, the present invention provides an improved means and method of forming a laid fibrous article characterized by a non-stepwise gradation of basis weight thereacross, which article is readily removable from a foraminous forming surface on which the same is formed.

The present invention provides an improved means and method for production of fibrous articles of the type having a non-stepwise gradation of basis weight, wherein the highest basis weight is provided forward of the lateral center line of the article as compared to the rear portion thereof, the central region along the length of the article has a higher basis weight than the peripheral or marginal, or wherein the article has a combination of these gradations of basis weights. Compared to conventional techniques, the method and apparatus of the invention more efficiently provides the desired non-stepwise gradations in the basis weight of the article. Other aspects and advantages of the present invention will be more fully apparent from the ensuing disclosure and appended claims.

BRIEF DESCRIPTION OF THE DRAWINGS

The invention will be more fully understood and further advantages will become apparent when reference is made to the following detailed description of the invention and to the drawings in which.

DETAILED DESCRIPTION OF THE PREFERRED EMBODIMENTS

Figure 1:
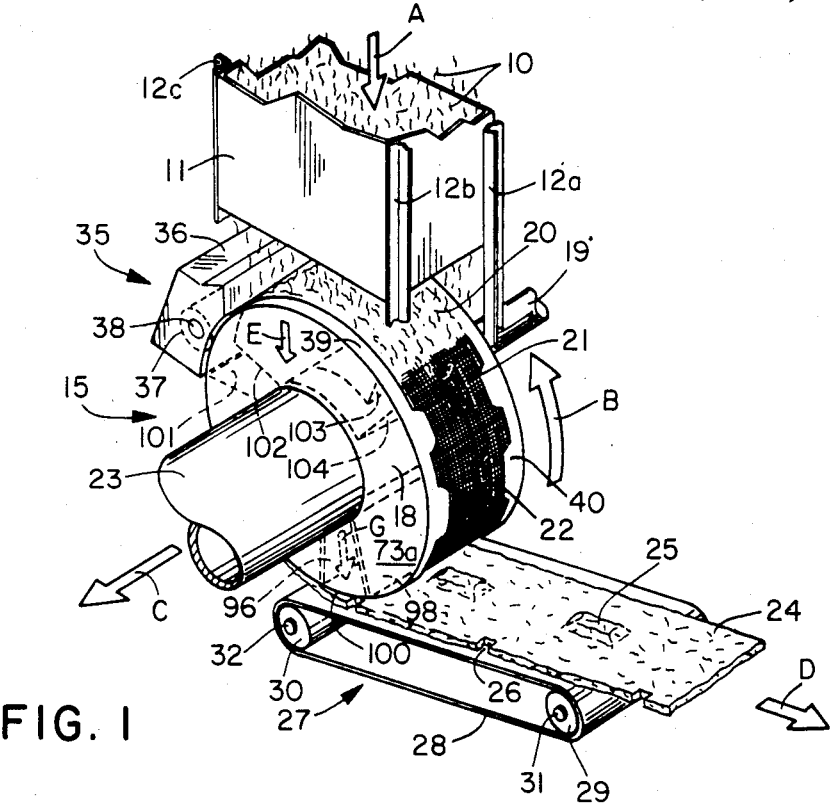
FIG. 1 is a schematic perspective view, with parts broken away, of apparatus for forming a laid fibrous article in accordance with one embodiment of the present invention.

Referring now to the drawings, FIG. 1 shows an apparatus suitable for forming a laid fibrous article in accordance with the present invention. Fibers 10, which enter the system as air-entrained fibers in a stream flowing in the direction indicated by Arrow A, may suitably be derived from a batt of cellulosic, e.g., wood pulp, fibers or other natural or synthetic fibers, which have been subjected to fiberization treatment, i.e., picked apart, in a manner known in the art to provide loose fibers. The fibers may be entrained in any other suitable gaseous medium, and references to air as the entraining medium herein will be understood to encompass all such other entrainment fluids.

The stream of air-entrained fibers passes by means of flow channel housing 11 to the forming drum assembly 15. The flow channel housing serves to direct and concentrate the air-entrained fibers and to provide a uniform velocity profile in the air/fibers stream. The flow channel housing is supported by support members 12a-c, which aggregately form a support frame for the housing and may be anchored and/or joined to other suitable structural elements as necessary or desirable.

The forming drum assembly 15 comprises a forming drum 18 which is rotatable in the direction of Arrow B. Rotation of the drum is affected by means of the forming drum drive shaft 19 which may be joined to suitable drive means (not shown) such as an electric or other motor directly or indirectly coupled to such shaft. The forming drum comprises an air-laid fibrous web laydown zone 20 positioned beneath the air/fibers flow channel housing 11 and configured as a vacuum laydown zone of the foraminous forming surface 21. This vacuum laydown zone constitutes a circumferential cylindrical surface portion of the rotatable drum. The vacuum laydown surface has imposed thereon a pressure differential under the action of vacuum suction means (not shown), such as an exhaust blower or other suitable suction means, which suctioningly withdraws air from the arcuate segment of the forming drum associated with the vacuum laydown surface through the air discharge (suction) duct 23, in a manner more fully described hereinafter. The foraminous forming surface 21 has therein a series of circumferentially spaced-apart, inverted, generally frusto-pyramidal shaped depressions or pockets provided by contoured surface portions 22 in the surface thereof, of elongate form with their longitudinal axes coincident with the center line of the foraminous forming surface 21, i.e., the surface portions 22 are centered on the forming surface relative to the cross-machine direction.

As described more fully hereinafter, the forming drum contains a series of radially extending wall members or baffles 101, 102, 103, 104, 98 and 96, which are stationary, as described modre fully in connection with FIG. 4 and FIG. 5 herein.

Thus, under the influence of vacuum suction means, air in the air-entrained fibers stream is drawn through the foraminous forming surface 21 into the interior of the forming drum, between baffle plate members 102 and 104, in the directions indicated by Arrow E, subsequently passing out of the drum through the discharge duct 23 in the direction of Arrow C. As the air-entrained fibers stream impinges on the forming surface 21, only the air component thereof is passed through and the fibers component of the stream is retained on the forming surface to form a nonwoven fibrous web thereon. Subsequently, with rotation of the drum, the formed web 24 is removed from the forming surface under the influence of gravity by the weight of the fibrous web 24 and with a pressure differential produced, for example, by pressurized air in blow-off zone 100, between baffle plate members 98 and 96, and flowing outwardly through the forming surface in the direction shown by Arrow G. The combination of the pressure differential across the forming surface at the annular blow-off zone 100, combined with the weight of the fibrous web 24 and the conformation of the contoured surface portions (depressions) 22, as hereinafter described, results in a readily removed fibrous web.

The web 24 is removed from the forming surface onto take-off conveyor 27 comprising endless conveyor belt 28 disposed about rollers 29 and 30, which are respectively positioned on roller shaft members 31 and 32. The longitudinally extending fibrous web as removed on the take-off conveyor 27 features a pad 25 corresponding to the concavely contoured surface portions 22 on the forming surface.

Figure 6:
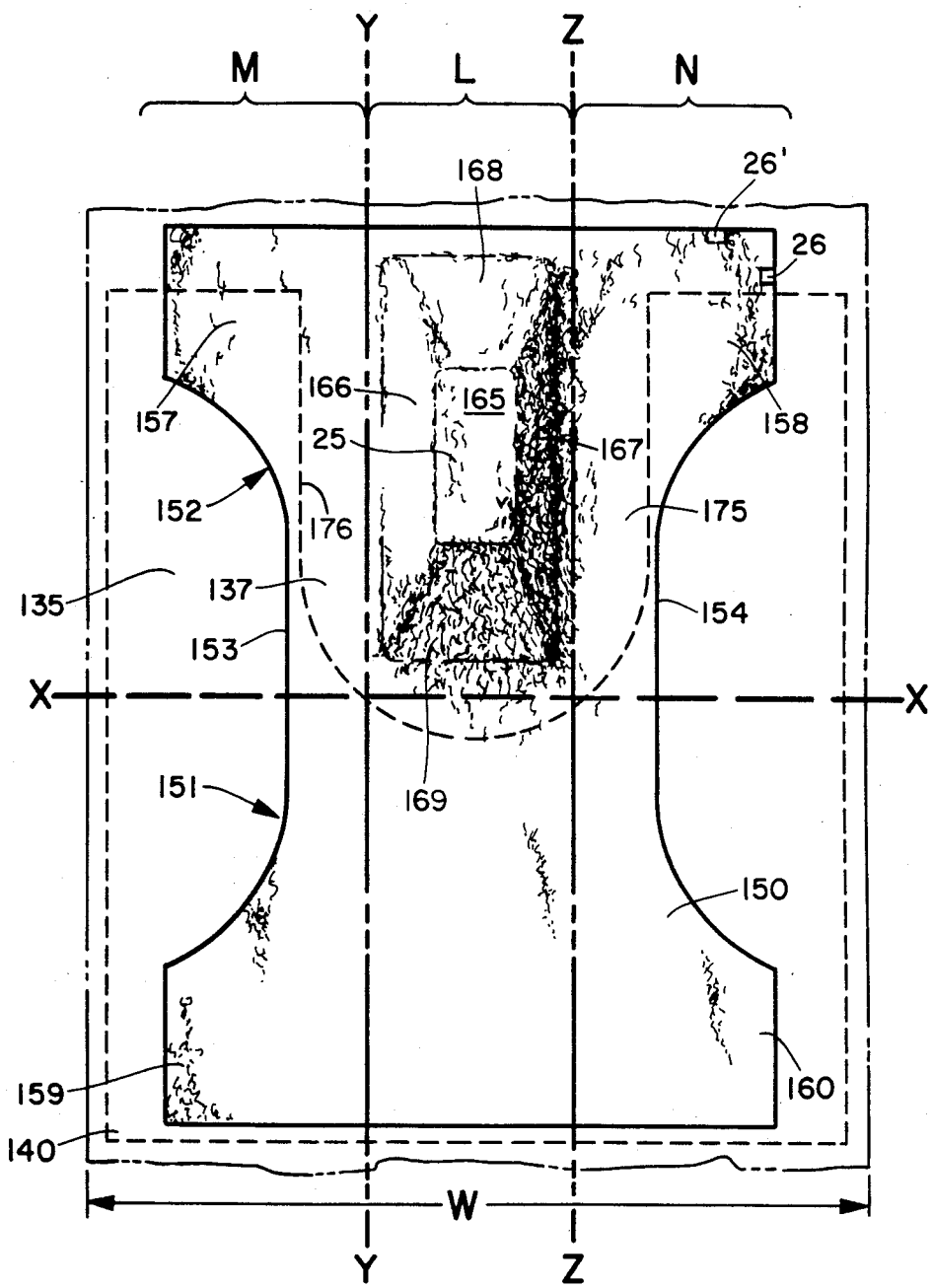
FIG. 6 is a plan view of a laid fibrous article produced by one embodiment of the apparatus and method of the present invention.

In addition to the blocking plate rings 39, the forming surface may also have disposed thereon symmetrically opposed arcuate blocking plates 40, as shown. These blocking plates are particularly advantageous when the forming drum assembly is employed to produce absorbent webs for use in disposable diapers and the like, whereby the blocking plates 40 prevent deposition of fibers on the forming surface to form corresponding arcuate cut-out sections on the finished web (not shown in FIG. 1, but as indicated in FIG. 6 by the edges 153, 154).

The longitudinally extending fibrous web 24 prior to its removal from the forming drum passes through the scarfing zone defined by the scarfing roll assembly 35. The scarfing roll assembly in turn comprises scarfing roll housing 36 containing scarfing roll 37 disposed on a scarfing roller shaft member 38, driven by means which for simplicity are not shown, but which may be any suitable motive means, and for example may involve coupling by gear or other means to the motor or drive means for the rotatable drum 18. The scarfing roll assembly constitutes trimming means for trimming the excess radial thickness of the laid fibrous web deposited on the forming surface 21 to yield a laid fibrous web having a substantially uniform, flat cross-direction contour on one major face surface thereof. The scarfing roll 37 is disposed in spaced adjacent relationship to the forming surface, and the scarfing roll and the forming surface are translated relative to one another in opposite directions, to remove excess thickness of the fibrous web. A transporting means, such as a suction fan, (not shown) draws the removed fibrous material away from the formed fibrous web and out from scarfing housing 36.

Thus, in the apparatus as shown in FIG. 1, the forming drum rotates in the direction shown by Arrow B, and the scarfing roll 37 moves in the same direction of rotation, thereby providing opposed movement of the roller surface relative to the surface of the drum proximate thereto, to remove excess thickness of the laid fibrous web. Alternatively scarfing roll 37 can be rotated to provide a co-directional movement of the roller surface relative to the surface of the forming drum most proximate thereto. In either situation, the rotational speed of scarfing roll 37 should be suitably selected to provide an effective scarfing and leveling action against the contacted surface of the formed fibrous web. In like manner, any other suitable means may be employed in place of the scarfing roll assembly 35 to provide a cutting or abrading action to the laid fibrous web by relative movement between the web (forming surface) and the trimming means.

Forming surface 21 constitutes the outer cylindrical surface of the forming drum 18 and features a non-flow region of the foraminous forming surface which may suitably be formed by blocking plate ring 39 or other suitable means that occludes the flow of gas through the forming surface. Such occlusion serves to prevent laydown of fibers on the forming surface when the stream of air-entrained fiberized fibers is flowed thereon with passage of the entraining gas therethrough. A contoured blocking ring 39 can be configured to form a key notches 26 on the finished laid fibrous web to provide sensing point for severing of the longitudinally extending fibrous web into discrete air-laid fibrous articles. Reference has been made in the preceding sentence to a longitudinally extending character of the fibrous web 24, and this will be understood to refer to the dimension or axis of the web in the direction indicated by Arrow D, whereby the longitudinal dimension is at right angles to the transverse or lateral dimension of the web (the lateral direction hereinafter being referred to also as the cross-machine direction, in contrast to the machine direction, which is the longitudinal direction).

Figure 4:
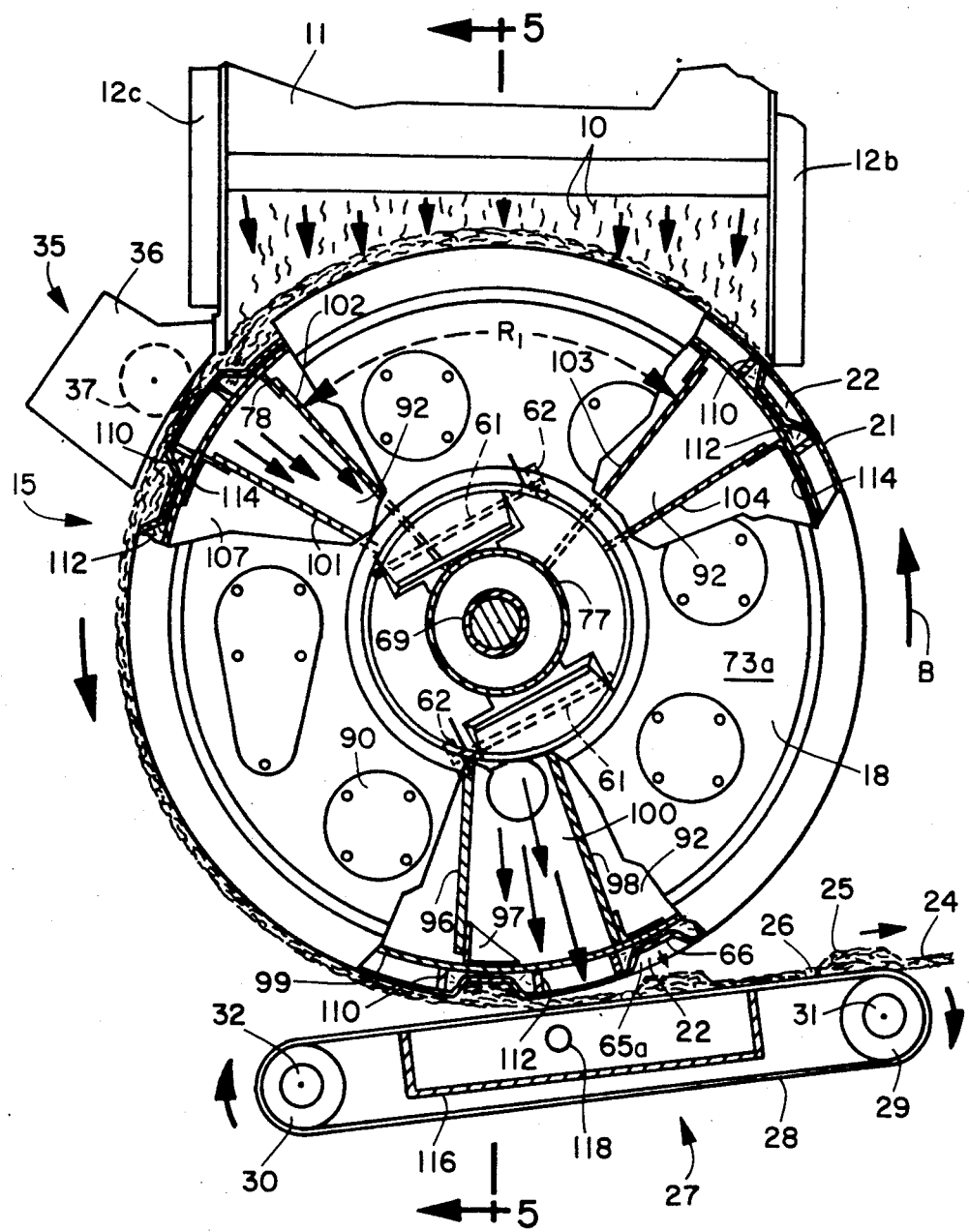
FIG. 4 is a partial sectional elevational view of the fibrous web-laying apparatus of FIG. 1, showing the construction of the interior compartments of the forming drum.
Figure 5:
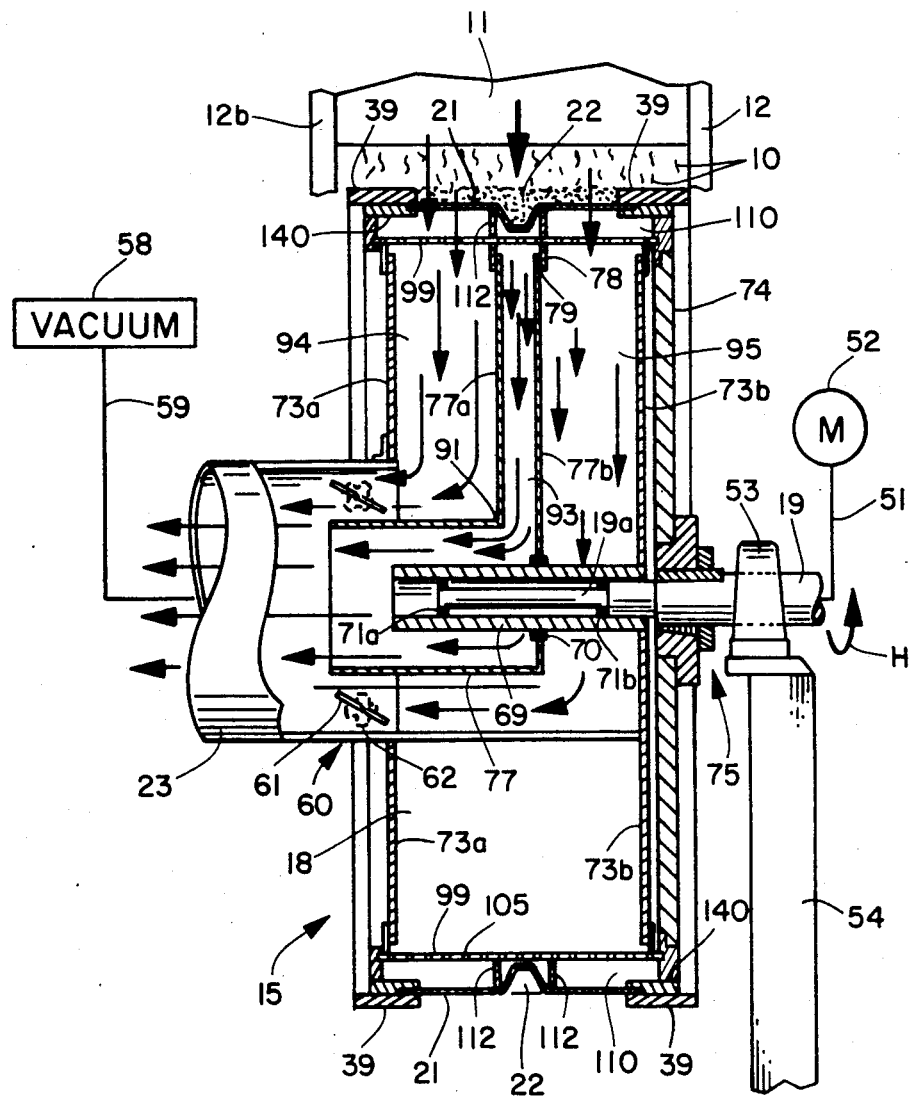
FIG. 5 is a cross-sectional elevational view of the apparatus of FIG. 4, taken along line 5—5 thereof.

The details of structure of the forming drum 18 are shown in FIGS. 4 and 5, FIG. 5 being a sectional elevational view of the forming drum assembly as shown in FIG. 4, along line 5—5 thereof. The specific structural elements shown in FIGS. 4 and 5 are numbered correspondingly with respect to the features shown in FIG. 1.

The forming drum assembly of this embodiment comprises a drum which rotates about a series of stationary baffles which present to the foraminous forming surface, a plurality of differential pressure zones.

As shown in FIG. 5, the drive shaft 19 for the forming drum is driven in the rotational direction indicated by Arrow H by forming drum drive means 52 coupled thereto by motive power transfer means 51, which in operation may constitute a gear drive, direct shaft coupling or other suitable means. The forming drum drive shaft 19 is disposed in a journal bearing 53 which in turn is associated with a journal bearing support member 54 to provide a support structure or the forming drum in operation.

The inner housing of the forming drum includes a spindle 69 which is cylindrically concentric with the drive shaft 19 and has associated therewith spindle seals 70 which provide for pressure sealing between the front and rear lateral vacuum passages 94 and 95 and the central vacuum duct passage 93, during rotation. The drive shaft 19 is coupled to and terminates in a forming drum drive shaft spindle section 19a, which is associated with shaft seal bearings 71a and 71b and optionally with seal rings, in a manner known in the art. The forming drum assembly includes stationary a front wall 73a and rotatable a rear drum wall 74. The drive shaft 19 is secured to the rear drum wall 74 by means of a bushing and mounting assembly 75, of conventional type.

The pressure differentials imposed on the foraminous forming surface 21 are generated by means of a vacuum source (suction) means 58, such as an exhaust fan, which is coupled to the forming drum structure via vacuum transfer coupling means 59 to the air discharge (suction) duct 23. Duct 23 has associated therewith a damper assembly 60 comprising damper plate 61, and damper modulating adjustment means 62, which may be employed to manually or automatically adjust the position of the damper plate, within the annular passage as shown, both above and below the forming drum central vacuum duct 77.

The forming drum, as shown in FIGS. 4 and 5, comprises a central vacuum duct 93, the walls 77a, 77b of which at their upper ends mate with a closure flange 78, with sealing means 79 provided by radially overlapping ends of the closure flange 78 and the upper walls 77a, 77b. The forming drum as shown in FIG. 4 features a series of circumferentially spaced-apart drum wall covers 90 for entry and maintenance of the interior space and apparatus of the forming drum assembly.

The interior space of the forming drum 18 comprises a high vacuum forming zone 93 which is in the form of an arcuate segment between the duct wall baffle 102 and the duct wall baffle 103, which are shown as radially extending, imperforate plates. Circumferentially and axially adjacent to the high vacuum forming zone 93 is low vacuum pressure zone 92, 94, 95 located between chamber wall baffle 104 and chamber wall baffle 101. This low pressure zone also extends between axially spaced-apart vacuum chamber walls 73a and 77a and between chamber walls 77b and 73b at zones 94 and 95, respectively. As a result, high vacuum zone 93 is nested within and, in the shown embodiment, is surrounded on four sides by the low vacuum zone.

Intermediate the circumferentially spaced-apart chamber wall baffles 96 and 98 is an optional pressure blow-off zone 100, which receives air under pressure (from a source not shown, but which may suitably be an exhaust stream from the vacuum suction blower fan), and serves the function of imparting an air flow, under positive pressure differential from the interior to the exterior side of the forming surface 21, to assist in removal of the laid fibrous web 24. As shown, the chamber wall baffle 96 is sealed in place to the inner drum ring 99 by a seal bracket 97. The inner drum ring 99, as shown in FIGS. 4 and 5, has a plurality of openings 105 (see FIG. 5) for accommodating the gas flows into, and out of, the forming drum. The inner drum ring 99 rotates in operation concurrent with the forming surface 21, to which same is attached. The inner drum ring nonetheless defines an interior region of the forming drum, which is sealed against the front and rear vacuum chamber walls 73a and 73b by closure flanges and seals analogous to flange 78 and seal 79 (as shown in FIG. 5). Between chamber wall baffle 96 and chamber wall baffled 101 is a third vacuum zone 107, and between chamber wall baffle 101 and duct wall baffle 102 is a low vacuum, passage region through which air is drawn from the scarfing zone constituted by scarfing roll assembly 35. A discrete amount of vacuum should be maintained within the third vacuum zone 107 and within the low vacuum, passage to retain the fibrous web against the foraminous forming surface 21. The discrete vacuum within these regions holds web 24 on the forming drum while the rotation of the drum transports the web toward conveyor 28.

Figure 3:
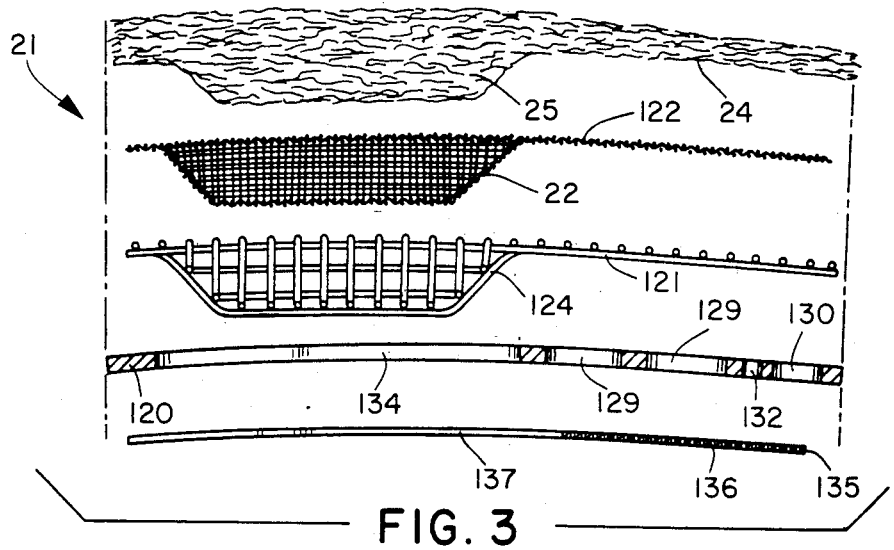
FIG. 3 is an exploded sectional elevational view of the forming surface of the FIG. 2, taken along line 3—3 thereof.
Figure 2:
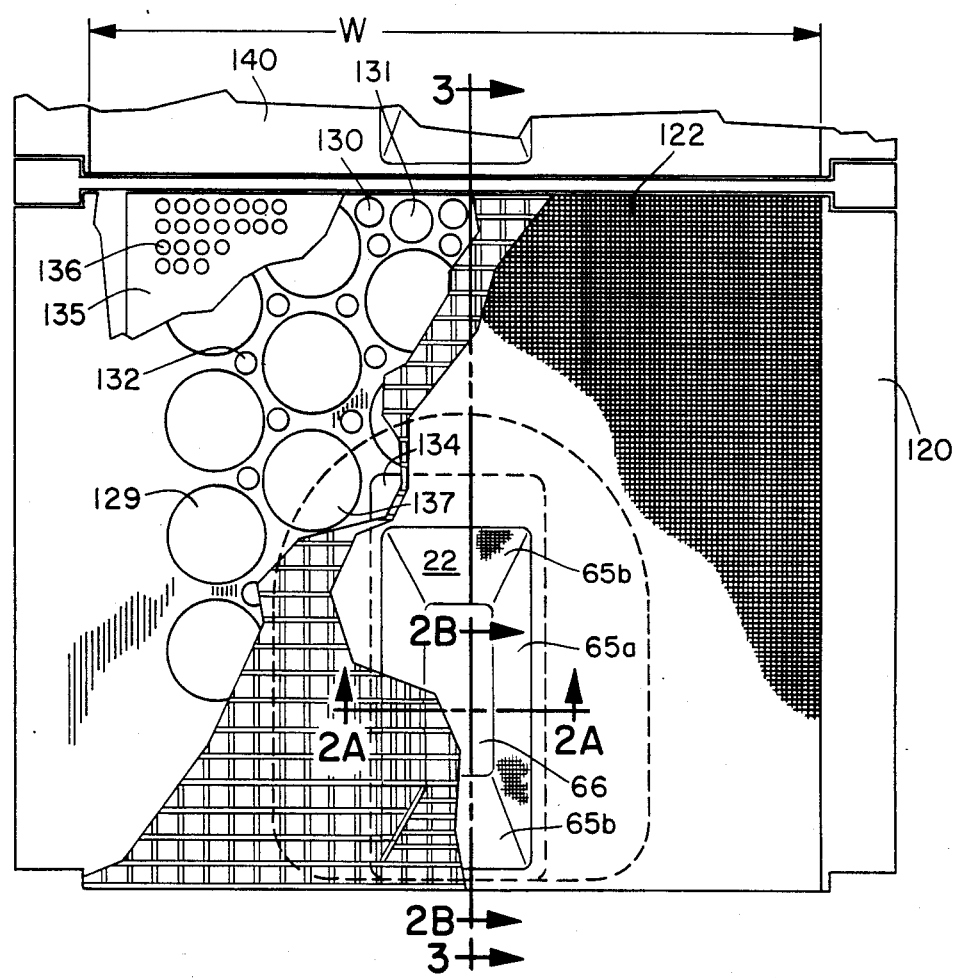
FIG. 2 is a partial sectional plan view of the foraminous forming surface, such as that of the FIG. 1 apparatus.

FIG. 2 shows a partial sectional plan view of the foraminous forming surface 21, illustrating the various components thereof. A corresponding exploded elevational view of the forming surface components is shown in FIG. 3, together with a section of the longitudinally extending fibrous web 24, containing pad 25 on its inner surface, shown in relationship to the forming surface elements.

The forming surface comprises a frame 120 having opening 134 therein to accommodate the concavely contoured surface portion of the forming surface. As shown, the frame has a plurality of openings therein, in addition to the opening 134, of varying size, from large frame openings 129, to intermediate large openings 131, to intermediate small openings 130, to small openings 132.

Disposed on the frame 120 is a support grid 121. The support grid contains a concavely contoured surface portion 124 bounded by longitudinal side and transverse end wall members 65a and 65b, respectively. Overlying the support grid 121 is screen 122 having a depression 22 formed therein corresponding to the concavely contoured surface portion 124. Finally, beneath the forming surface, as constituted by frame 120, screen 122 and support grid 121, is vacuum blocking plate 135 having a major opening 137 therein to accommodate the concavely contoured surface portion of the forming surface. Blocking plate 135 also has perforations 136 therein which may be, as shown, uniformly arranged across the blocking plate surface in a regular array.

The forming surface as shown thus is made up of a series of circumferentially extending and radially adjacent elements supported on frame element 120. In the aggregate, these elements form an air-laid web forming path 140 having a width W and extending around the entire peripheral cylindrical surface of the forming drum.

Figure 2A:
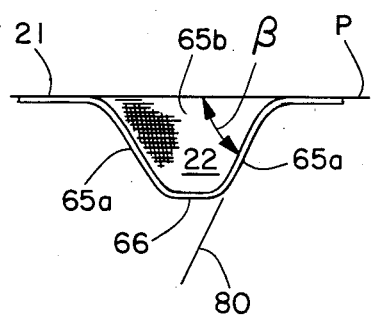
FIG. 2A is a sectional elevational view along line A—A of FIG. 2, showing the concavely contoured surface portion of the forming surface and illustrating the measurement of the wall angle for the side wall thereof.
Figure 2B:
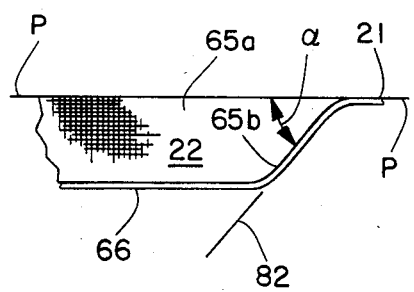
FIG. 2B is a sectional elevation view along line B—B of FIG. 2, showing the concavely contoured surface portion of the forming surface and illustrating the measurement of the wall angle for the end wall thereof.

The foraminous forming surface 21 has, as previously indicated, a plurality of circumferentially spaced-apart, centrally (in the cross-machine direction) aligned, concavely contoured surface portions (depressions) 22 formed thereon, as shown in FIGS. 4 and 5. As best seen in FIGS. 2, 2A and 2B, concavely contoured surface portions 22 are bounded by longitudinal side wall members 65a, transverse end wall members 65b, and a radiused base wall member 66 which is disposed at least appoximately parallel to the plane of the adjacent portion of foraminous forming surface 21. The longitudinal side wall members 65a and transverse end wall members 65b are angularly oriented with respect to the plane of the forming surface 21 proximally adjacent the concavely contoured surface portion 22, to define an included angle therebetween of not more than about 70°. Preferably this included angle is from about 45° to 68°. Thus, the included angle between respective longitudinal side wall members 65a and the plane P of the portion of forming surface 21 which is proximally adjacent thereto is measured by the angle beta in FIG. 2A. Similarly, the included angle between respective transverse end wall members 65b and the plane P of the portion of forming surface proximally adjacent thereto is measured by the angle alpha in FIG. 2B.

The side wall angle, beta, is measured between the side wall surface (extending by straight line 80 in FIG. 2A) and the plane P of the forming surface proximally adjacent the concavely contoured surface portion 22. As used herein, the term "forming surface proximally adjacent the concavely contoured surface portion" refers to the surface portion 21 that is adjacent to the concavely contoured surface portion 22 but is not in any way deformed as part of or an extension of the contour of the concave surface portion 22. The term "concavely contoured" as used in such context refers to the fact that the forming surface has a depression therein which under air-laying fiber deposition conditions will result in the formation of a protrusional area on the air-laid fibrous web. In like manner, as shown in FIG. 2B, the end wall member 65b has an angle of orientation, alpha, which is measured between the end wall member 65b (extended by straight line 82) and the plane P of the forming surface proximally adjacent the concavely contoured surface portion.

In the present invention, the wall angles alpha and beta should each be not more than about 70°, and preferably, should each be in the range of from about 45° to 68° to effect improved releasability of the fibrous web from the forming surface. The angles alpha and beta may be, but need not be, identical. For example, good releasability characteristics have been obtained in practice where the angle beta is approximately 65° and the angle alpha is approximately 45°, with the concavely contoured surface portion 22 being of generally inverted frusto-pyramidal shape. Nonetheless, it is to be recognized that numerous other shapes and conformations for the concavely contoured surface portion may be employed to good advantage, other than the generally inverted frusto-pyramidal shape of elongate form which is shown in the illustrative drawings. For example, conical or oblate conical openings could be employed, in addition to any other wall shapes and orientations meeting the side wall angle criteria hereof.

In the specific embodiment shown in the drawings, wherein the concavely contoured surface portion 22 is elongate in shape and its bounding walls comprise longitudinal side wall members 65a and transverse end wall members 65b joined at their bottom edges to a base wall member 66, it is preferred that the included angles beta of the longitudinal side walls 65a are between about 55° to 68° and the included angles alpha of the transverse end walls 65b are between about 45° and 60°.

In the forming surface section shown in FIG. 2, the vacuum blocking or attenuating plate 135 is positioned in closely spaced registration with, and transverse to flow of gas through, the forming surface, for diminution of the pressure differential exerted on the forming surface in register with the vacuum attenuating plate, whereby a reduced basis weight of fibrous material is deposited on such forming surface region. The vacuum attenuating plate may, as shown in FIG. 2, have an opening or hole therethrough which is sized and configured to accommodate the placement of the concavely contoured surface portion therein. Alternatively, the vacuum attenuating plate may, as shown in FIG. 6, be generally U-shaped with its inner edge circumjacent to bounding walls of the concavely contoured surface portion.

The apparatus of FIGS. 1-5 thus illustrates a rotatable cylindrical drum whose outer circumferential wall surface comprises the forming surface, with a plurality of concavely contoured forming surface portions 22 circumferentially spaced apart thereon, and a plurality of radially extending, stationary baffles and walls disposed in the interior of the rotatable cylindrical drum to divide the interior into plural arcuate segments communicating with respective differential pressure zones on the forming surface. A pneumatic flow means defines pressure differential zones on the forming surface and imposes a pressure differential thereon. The pneumatic flow means comprises a vacuum suction means joined in gas flow communication with a first arcuate segment in the cylindrical drum. The first arcuate segment defines a vacuum laydown zone on the forming surface, and the vacuum suction means draws air through the vacuum laydown zone on the forming surface, into the first arcuate segment and out of the rotatable cylindrical drum. Such apparatus can further comprise means for diverting a portion of the flow of air drawn through the vacuum laydown zone on the forming surface into the first arcuate segment, under positive pressure into a second arcuate segment defining a pressurized take-off zone for removal of the laid fibrous article from the forming surface.

As shown in FIGS. 4 and 5, the walls 77a, 77b bound the generally wedge shaped, central duct 91, which forms the high vacuum forming zone 93 constituting an arcuate segment of the rotatable cylindrical drum. The walls are of arcuate shape and are disposed in transversely spaced relationship to one another to divide the first arcuate segment into transverse subsegments 94, 93 and 95 defining corresponding vacuum laydown subzones on the forming surface. Flow restriction means comprised of the damper assembly 60 is interposed between the vacuum suction means 58 and the two outer vacuum laydown subzones of the forming surface, 94 and 95, for effecting a transversely varying differential pressure on the forming surface vacuum laydown zone, whereby the laid fibrous article has a transversely varying basis weight (i.e., in the cross-machine direction).

In contrast to the specific embodiment shown in FIG. 5, wherein the respective front and rear walls of the central vacuum duct 91 (arcuate walls 77a and 77b) transversely divide the vacuum laydown zone into differential pressure subzones, it may be suitable in other applications of the present invention to utilize a greater or lesser number of arcuate baffles to define a correspondingly greater or lesser number of transverse subzones of the forming surface, in combination with flow restriction means disposed between the forming surface subzones and the vacuum suction means in correspondingly greater or lesser numbers, but in all instances where such cross-machine basis weight differential of the laid fibrous web is desired, flow restrictions will be interposed between at least one of the forming surface vacuum laydown subzones and the suction means. Alternatively, in some instances of the present invention, it may be desirable to provide a corresponding variation of basis weight in the formed fibrous article with the highest basis weight in the outer longitudinal sections of the fibrous web, and accordingly flow restriction means may be associated with the central gas flow passage to provide a reduced longitudinally extending central basis weight region relative to the outer longitudinally extending regions of the fibrous web corresponding to the peripheral gas flow passages. In the FIG. 5 apparatus, the flow restriction means, in the form of a damper assembly 60 have been disposed between the transversely outer forming surface laydown subzones and the vacuum suction means.

In operation, the air-laid fibrous web is formed from a stream of air-entrained fiberized fibers, by flow of the entrainment gas through the openings in the foraminous forming surface 21 and into the chambers constituting the vacuum forming zones 92-95 in the rotatable drum 18, with suction also being applied to the resulting laid fibrous web in the vicinity of a scarfing zone defined by the location of the scarfing roll assembly 35 and the scarfing housing 36.

In a particular aspect of the invention, chamber wall member 101 is selectively moveable within forming drum 18 along the circumferential direction thereof. The movement of wall member 101 can advantageously be employed to regulate the amount of vacuum applied to the drum-side surface of the portion of fibrous web 24 which is located in the scarfing zone under housing 36. For example, with respect to FIG. 4, a clockwise repositioning of wall member 101 would decrease the amount of vacuum applied to the fibrous web, and a counter-clockwise repositioning of the wall member would increase the amount of vacuum applied to the fibrous web. If an excessive amount of vacuum is applied to the portion of web 24 within the scarfing zone, the fibrous material trimmed away by the scarfing roll can be redeposited onto the web instead of being withdrawn out of housing 36.

The inflows of air to the arcuate segment constituting high vacuum forming zone 93 and the low vacuum zone 92, 94, 95 are exhausted from the forming drum in air discharge duct 23, under the influence of vacuum suction by vacuum means 58. Concurrently, the drum rotates to pass the air-laid fibrous web on the forming surface from the vacuum laydown zone to the scarfing zone where excess thickness of the fibrous web is trimmed to a predetermined extent, following which the air-laid fibrous web moves past the intermediate vacuum zone 107 (FIG. 4) and finally to an optional pressure blowoff zone 100. In blow-off zone 100, air is introduced under pressure and directed radially outwardly against the fibrous web on the forming surface portion circumferentially aligned therewith, whereby the gas pressure and the specifically contoured surface portion 22 effects a ready release of the fibrous web from the forming surface, without binding or sticking of the air-laid fibrous web in the depressions 22, such as would adversely impact the normal operation of the apparatus, and potentially necessitate shut-down and manual removal of the fibrous web from the forming surface. In an alternative configuration of the apparatus of the invention, a vacuum suction box 116 can be located below conveyor belt 28 to help remove web 24 from the forming surface 21. Vacuum box 116 opens onto belt 28, and a suction of air out of the vacuum box through outlet opening 118 draws an air flow through perforations in the conveyor belt. This flow of air, in turn, operates to draw web 24 away from the forming surface. Vacuum box 116 can be employed with or without the use of positive pressure in blow-off zone 100.

The annular space between the inner ring 99 and the forming surface 21 is circumferentially sealed by various circumferentially spaced, radial sealing members to preserve the pressure differentials in the various differential pressure zones of the forming assembly. More particularly, a plurality of transverse sealing members 110 connect in sealing engagement between inner ring 99 and forming surface 21, and also connect in sealing engagement between drum walls 73a and 74. These transverse sealing members substantially prevent the movement of ambient air through the annular space between inner ring 99 and forming surface 21 and into the low and high vacuum zones.

To better segregate the high vacuum zone from the low vacuum zone, circumferential sealing members 112 can optionally be located in the annular space between inner ring 99 and forming surface 21. Pairs of sealing members 112 are axially spaced apart and are located adjacent to both longitudinal side wall members of the contoured surface depressions 22. The circumferential sealing members connect in sealing engagement with transverse sealing members 110 and operate to reduce cross flow between the high vacuum zone and the low vacuum zone along a path through the annular space.

To further reduce the intrusion of ambient air into the differential vacuum zones, sealing flange members 114 are connected to chamber wall baffles 101 and 104, and are arranged to contact inner ring 99 with a slideable, sealing engagement. Flange members 114 extend axially across the width dimensions of chamber wall baffles 101 and 104, and have a circumferentially extending length dimensions which are at least equal to the circumferential distance between consecutive transverse sealing members 110. The above-mentioned length dimensions refer to the portions of flange members 114 that slideably contact ring 99. As illustrated in FIG. 4, the slideable portions of flange members 114 are arranged to extend circumferentially away from housing 11. Thusly configured, flange members 114 substantially prevent the intrusion of ambient air along a path that extends through ring 99, around the edge of transverse sealing member 110, back through ring 99, around the edge of chamber wall baffle 101 or 104, and back again through ring 99 into the vacuum zones.

The concavely contoured surface portions in accordance with the present invention are bounded by walls which preferably define inclination angles of from about 45° to 68°. At wall angles greater than about 70°, the angle of inclination of the walls relative to the forming surface proximally adjacent thereto, is so great that the fibrous web protrusions formed thereby do not readily disengage from the forming surface, unless very high pressure gas streams are directed against the foraminous forming surface in the vicinity of such contoured portions. On the other hand, at wall angles below 45°, the gradation in basis weight associated with the concavely contoured surface portion may be too low to provide the high basis weight which is required when the fibrous web is employed for applications such as disposable diapers or sanitary napkins.

FIG. 6 shows a plan view of a laid fibrous article, which is formed by the apparatus illustrated in FIGS. 1-5. This fibrous article is particularly suitable for use in a disposable diaper. The air-laid article is shown in the drawing as referenced to the width W of the air-laid web forming path 140 and the vacuum blocking plate 135, the profiles of which are shown in dotted line representation for ease of reference. The air-laid fibrous web article 150 is shown with a lateral center line X—X, and is formed from the longitudinally extending web 24 as shown in FIG. 1, by severing the web 24 transversely into suitable lengths, as described hereinafter in greater detail. The fibrous web article 150 has a rear section 151, posterior to the center line X—X and a front section 152 anterior thereto. As mentioned previously this fibrous web article features leg cut-outs defined by edges 153, 154, resulting from the utilization of the arcuate blocking plates 40 as shown in FIG. 1. The key notch 26 formed by the non-flow region associated with blocking plate 39 in FIG. 1 is located at a side edge of the front section of the fibrous web article; an alternative position for the open area is shown at 26′. Such notch or "key" is employed as a reference point for severing the longitudinally extending fibrous web into lengths of predetermined dimension.

The longitudinal central zone L of the fibrous web article provides a higher basis weight region of the article relative to zones M and N on either side thereof. The respective lines Y and Z demarcating the successive longitudinal zones define the general, approximate locations of fold-lines, along which the fibrous web article may be folded for storage and packaging purposes. The longitudinal peripheral zones correspond to the outer forming surface subzones overlying vacuum passages 94 and 95 as shown in FIG. 5, with the central longitudinal zone L corresponding to vacuum passage 93 in FIG. 5.

Each of the longitudinal peripheral zones M, N has associated therewith laterally extending corner segments or "ears" with the front section 152 having left-hand and right-hand ears, 157 and 158 respectively, with rear section 151 having associated therewith corresponding ears 159 and 160. Positioned in the central longitudinal zone L of the front section 152 is an integral pad 25, corresponding to the protrusion formed on the longitudinal extending web in the operation of the apparatus shown in FIGS. 1-5. Pad 25 comprises a frusto-pyramidal, non-separable protrusion from the fibrous article's top surface, corresponding to the concavely contoured surface portion of the forming surface. Pad 25 features a pad top surface 165 which is substantially flat and corresponds to the base wall member 66 of the forming surface 21. The pad side surfaces 166 and 167 correspond to the side walls of the concavely contoured surface portion, and the pad end surfaces 168, 169 correspond to the end wall members of the concavely contoured forming surface portion.

A high basis weight region 175 extends transversely across the longitudinal zones M, L and N generally in the front section of the fibrous web article, and its boundary is demarcated by and corresponds to the edge 176 of the vacuum blocking plate 135, whereby the basis weight of the material surrounding pad 25 is higher than the ear regions 157, 158 in the front section of the fibrous article and is higher than the basis weight of the rear section 151 of the fibrous article, with the exception of the small arcuate segment extending centrally longitudinally for a short distance posterior of the lateral center line X—X.

In the preferred practice of the present invention, the vacuum laydown zone has subzones which are situated and arranged to provide a lower pressure differential in the peripheral forming surface subzones defined by vacuum passages 94, 95 relative to the central subzone 93, and the blocking plate is configured to provide approximately 65% of the weight of the fibrous article in the front section 152 of the laid article and approximately 35% of the weight in the rear section 151 thereof. Such a fibrous article is highly advantageous in disposable diaper service.

Figure 7:
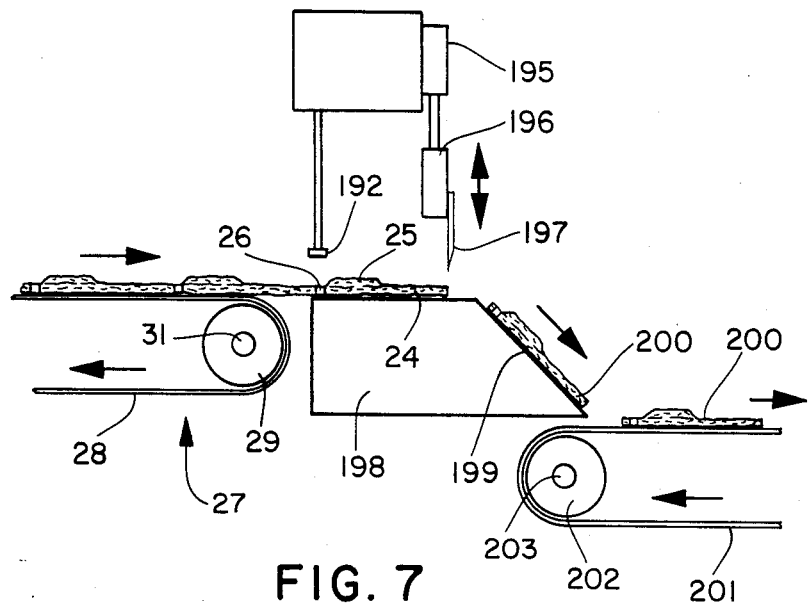
FIG. 7 is a schematic diagram of a portion of a discrete fibrous article-forming system, located downstream of the apparatus shown in FIG. 1, wherein the longitudinally extending fibrous web is severed into discrete fibrous articles.

It will be readily apparent that various conventional devices and techniques can be employed to sever fibrous web 24 into predetermined lengths to provide selected laid fibrous articles. For example, FIG. 7 shows a schematic diagram of a representative apparatus which may be utilized downstream of the apparatus shown in FIGS. 1–5 to provide laid fibrous articles of predetermined length as derived from the longitudinally extending fibrous web 24.

As illustrated, the longitudinally extending fibrous web 24 is transferred from take-off conveyor 27, comprising endless belt 28 rotated by conveyor roller 29 under the influence of motive drive means coupled to roller shaft 31, to a transverse severing assembly. The longitudinally extending web 24 with surface protrusion formed by pad 25 thereon passes onto the top flat surface of a web severing station 198. A mechanical or electronic sensor means 192 detects key notches 26 within web 24 and triggers an actuator 195 which moves a reciprocating blade assembly 196. Blade assembly 196 carries blade member 197 in a cutting action against selected regions of web 24, thereby transversely severing the web into discrete articles 200. After severing, the discrete laid fibrous articles 200 pass via a downwardly inclined discharge surface 199 to an endless conveyor belt 201 which is driven by roller 202 mounted on shaft 203 in turn driven by suitable drive means (not shown) such as an electric motor.

Figure 8:
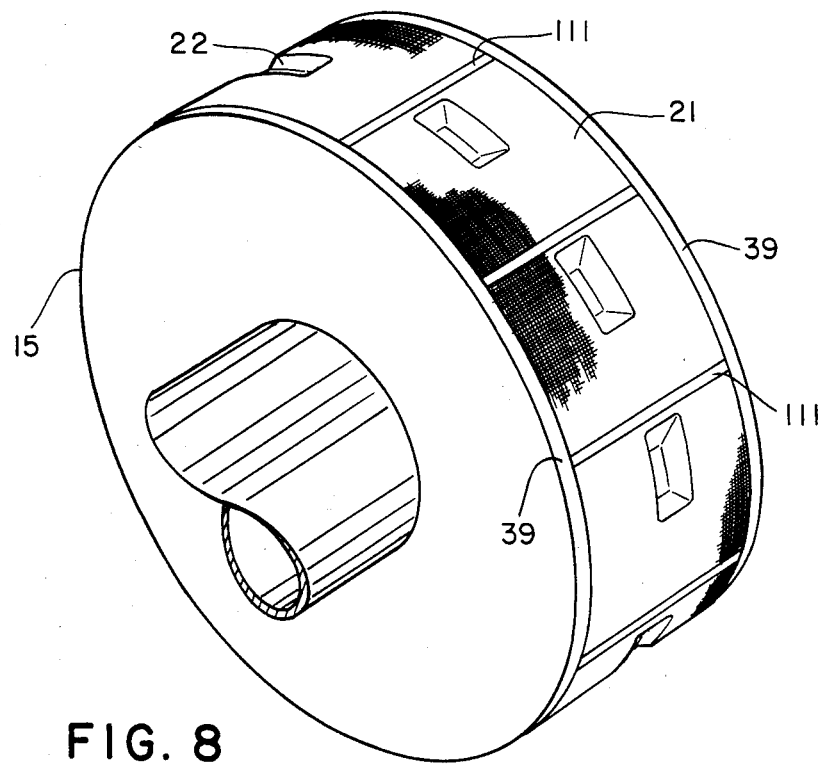
FIG. 8 is a schematic perspective view of a further embodiment of the invention, which employs blocking bar members across the forming surface.

In another embodiment of the invention, the discrete fibrous articles 200 can be directly formed on forming surface 21. As representatively shown in FIG. 8, a plurality of blocking bar members 111 can be located at selected locations along the circumference of the forming surface. Bar members 111 interconnect between blocking rings 39 and are generally aligned along the axial dimension of forming drum 15. These bar members also overlie forming surface 21 and block the accumulation of fibers along relatively narrow, transverse portions of the forming surface. As a result, the deposition of fibers onto forming surface 21 can create a substantially non-continuous web comprised of individual, discrete fibrous articles 200.

The efficacy of a specific embodiment of the present invention is shown with reference to the following Example, which demonstrated the operation of the apparatus and method described hereinabove. The stated materials, proportions and parameters are exemplary, and are not intended to specifically limit the scope of the invention.

EXAMPLE

In a series of tests, the performance of the forming drum was demonstrated by a forming surface segment having a radius of curvature for the forming surface proximally adjacent the concavely contoured surface portion, of 28.375 inches (72.1 cm), and with a radius of curvature for the base wall member 66 of the concavely contoured surface portion of 26.5 inches (67.3 cm). The forming surface segment thus spanned an arcuate segment of 30 degrees, with the base wall member 66 of the concavely contoured surface portion being 2.5 inches (6.4 cm) long, and the mouth of the concavely contoured surface portion being 6.5 inches (16.5 cm) long, as measured in the machine direction in the plane of the forming surface proximally adjacent thereto. The end wall member 65b at each end of the elongated frustopyramidal shaped depression was 3.0 inches (7.62 cm) at the mouth of the depression, tapering down to approximately 1 inch (2.54 cm) at the intersection of the end wall with the base wall member 66 of the concavely contoured surface portion. The base wall member of the depression thus was 3.0 inches (7.62 cm) in length and approximately 1.75 inch (4.44 cm) in width. (Note: all dimensions referenced are planar surface dimensions, and are exclusive of curvate end segments of the wall members and base wall member, which typically had radii of curvatures at their intersections of 0.25–0.5 inch (0.6–1.3 cm).

In a series of comparative tests (Run A) of a structure not in accordance with the present invention, a forming segment was used which had a concavely contoured surface portion 22 with the included angle beta of the side wall being 81.5 degrees and the included angle alpha of the end wall being 49 degrees. A fibrous web of cellulosic fibers then was deposited on the forming surface, including the concavely contoured surface portion, and the release efficiency was measured by slow-motion photography utilizing 61 separate laydowns, each of which was attempted to be removed by gravational fall-off of the web from the concavely contoured surface portion when same was arranged with the open face of the depression overlying the receiving surface (corresponding to the position of the forming surface at pressure blow-off zone 100).

A second test (Run B) was conducted, using a forming section having a concavely contoured surface 22, in accordance with the present invention, but otherwise identical to that of Run A, so that all dimensions of the concavely contoured surface portion were identical to those of Run A, with the exception that the side wall angle beta was 65 degrees and the end wall angle alpha was 45 degrees. Again, 61 laydowns were made and the percentage release efficiency, % E, of each of Runs A and B was determined by dividing the number of successes, S, wherein the laid web freely released without binding or sticking, by the number of trials, T, and multiplying by 100. Thus, % E = S/T × 100.

The Run A design failed to release in 11 of the 61 trials, with three trials exhibiting failure to release in the rear, two exhibiting failure to release in the front, and six failing to release on the sides, yielding an efficiency of 82% (50 successful trials out of 61). In contrast, Run B, representative of the present invention, yielded 100% release efficiency with complete release in 61 out of the 61 trials.

Accordingly, the apparatus and method of the present invention, wherein the concavely contoured surface portion of the forming surface has side walls with angles of from about 45° to 68°, provides a high degree of releasability of the laid fibrous article from the forming surface, consistent with the objective of imparting a raised surface of high basis weight. The readily removable character of the laid fibrous article from the concavely contoured surface portions of the forming surface of the present invention renders such forming surface highly attractive in automated high-speed commercial operation for the manufacture of fibrous web articles.

Although various preferred embodiments have been described hereinabove as illustrative of the present invention, it is to be appreciated that other variants, modifications and embodiments are possible, and all such apparent variations, modifications and embodiments are to be considered as being within the spirit and scope of the present invention.

What is claimed is:

1. A method for forming a fibrous article, comprising the steps of:
   providing a rotatable cylindrical drum, an outer circumferentially extending cylindrical wall surface of which is comprised of a foraminous forming surface;
   defining an annular space between said forming surface and an inner ring, which rotates with said forming surface and is capable of passing air therethrough;
   substantially preventing a circumferential movement of air through said annular space with a plurality of circumferentially spaced, transverse sealing members, said transverse sealing members connected in said annular space in sealing engagement between said inner ring and said forming surface;
   dividing the interior of said drum into plural arcuate segments with a plurality of radially extending stationary baffles, said arcuate segments defining and communicating with respective differential pressure zones on said forming surface, and said differential pressure zones including a vacuum laydown zone located on a portion of said forming surface over a first of said interior arcuate segments;
   substantially preventing an intrusion of ambient air around an edge of said baffles with a sealing flange member which contacts said inner ring with a slideable, sealing engagement and which extends axially across a width dimension of said baffle and extends circumferentially with a length at least equal to a circumferential distance between consecutive transverse sealing members;
   drawing air through the vacuum laydown zone on the forming surface into the first arcuate segment and out of the rotatable drum; and
   depositing fibers onto said forming surface under the influence of said air drawn through said vacuum laydown zone.

2. A method as recited in claim 1, further comprising the step of providing a concavely contoured portion in the forming surface, wherein the concavely contoured surface portion is bounded by walls angularly oriented with respect to the plane of the forming surface proximally adjacent the concavely contoured surface portion, to define an included angle therebetween of from about 45° to 68°.

3. A method according to claim 2, wherein the concavely contoured surface portion is of generally inverted frusto-pyramidal shape.

4. A method according to claim 3, wherein the concavely contoured surface portion is elongate in shape, and its bounding walls comprise longitudinal side walls and transverse end walls joined at their bottom edges to a base wall member.

5. A method according to claim 4, wherein the included angles of the longitudinal side walls are between about 55° and 68°, and the included angles of the transverse end walls are between about 45° and 60°.

6. A method as recited in claim 1, further comprising the step of segregating high and low vacuum zones within said annular space between the inner ring and the forming surface.

7. A method as recited in claim 6, wherein
   said high and low vacuum zones are segregated with circumferentially extending, axially spaced sealing members, which are connected in said annular space in sealing engagement with said transverse sealing members to reduce cross flow between said high and low vacuum zones.

8. A method according to claim 1, further comprising diminishing the pressure differential on a predetermined portion of the forming surface, whereby a reduced basis weight of fibrous material is deposited on such portion of the forming surface.

9. A method according to claim 8, further comprising dividing the first arcuate segment into transverse subsegments defining corresponding vacuum laydown subzones on the forming surface, restricting gas flow through at least one of the forming surface vacuum laydown subzones, for effecting a transversely varying differential pressure on the forming surface vacuum laydown zone, whereby the laid fibrous article has a transversely varying basis weight.

10. A method according to claim 9, wherein the first arcuate segment is divided into three transverse subsegments defining corresponding vacuum laydown subzones on the forming surface and wherein the gas flow rate is restricted through the transversely outer forming surface vacuum laydown subzones.

11. A method according to claim 1, further comprising diverting a portion of the air drawn through the vacuum laydown zone on the forming surface into the first arcuate segment, under positive pressure into a second arcuate segment defining a pressurized take-off zone for flow through the forming surface in a direction opposite to flow of gas through the forming surface in said vacuum laydown zone, to effect removal of the laid fibrous article from the forming surface.

12. A method according to claim 1, further comprising abradingly trimming an excess thickness of a laid fibrous web deposited on the forming surface to yield of a substantially uniform predetermined thickness of said laid fibrous web.

13. An apparatus for forming a laid fibrous article, comprising:
- a foraminous forming surface for depositing fibers under the influence of a pressure differential imposed on the forming surface;
- a rotatable cylindrical drum, an outer circumferentially extending cylindrical wall surface of which is comprised of said forming surface;
- an inner ring which is capable of passing air therethrough and which is connected to rotate with said forming surface and define an annular space therebetween;
- a plurality of circumferentially spaced, transverse sealing members connected in said annular space in sealing engagement between said inner ring and said forming surface;
- a plurality of radially extending, stationary baffles sealingly disposed in the interior of said rotatable cylindrical drum to divide the interior into plural arcuate segments, said segments defining and communicating with respective differential pressure zones on the forming surface, and said differential pressure zones including a vacuum laydown zone located on a portion of said forming surface over a first of said interior arcuate segments;
- a sealing flange member connected to a selected stationary baffle and arranged to contact said inner ring with a slideable, sealing engagement, said sealing flange member extending axially across a width dimension of said stationary baffle and extending circumferentially with a length which is at least equal to a circumferential distance between consecutive transverse sealing members; and
- pneumatic flow means comprising vacuum suction means joined in gas flow communication with said first arcuate segment in said rotatable cylindrical drum for drawing air through the vacuum laydown zone on the forming surface into the first arcuate segment and out of the rotatable cylindrical drum.

14. An apparatus as recited in claim 13, wherein said forming surface includes a plurality of concavely contoured forming surface portions circumferentially spaced apart on said forming surface.

15. An apparatus as recited in claim 14, wherein said concavely contoured surface portion of the forming surface is bounded by walls angularly oriented, with respect to the plane of the forming surface proximally adjacent the concavely contoured surface portion, to define an included angle therebetween of from about 45° to 68°, whereby the laid fibrous article is readily removable from the forming surface.

16. An apparatus as recited in claim 14, further comprising a pair of axially spaced, circumferential sealing members, said circumferential sealing members located in said annular space adjacent to longitudinal side wall members of said concavely contoured forming surface portions and connected in sealing engagement with said transverse sealing members, and said circumferential sealing members operable to reduce cross flow through said annular space.

17. Apparatus according to claim 14, wherein the concavely contoured surface portion is of a generally inverted frusto-pyramidal shape.

18. Apparatus according to claim 17, wherein the concavely contoured surface portion is elongate in shape, and its bounding walls comprise longitudinal side walls and transverse end walls joined at their bottom edges to a base wall member.

19. Apparatus according to claim 18 wherein the included angles of the longitudinal side walls are between about 55° and 68°, and the included angles of the transverse end walls are between about 45° and 60°.

20. Apparatus according to claim 13, further comprising a vacuum attenuating plate positioned in closely spaced registration with, and transverse to flow of gas through, the forming surface, for diminution of the pressure differential exerted on the forming surface in register with the vacuum attenuating plate, whereby a reduced basis weight of fibrous material may be deposited on the forming surface in register with said vacuum attenuating plate.

21. Apparatus according to claim 20, wherein the vacuum attenuating plate is generally U-shaped, with its inner edge circumjacent to bounding walls of the concavely contoured surface portion.

22. Apparatus according to claim 13, further comprising means for diverting a portion of the air drawn through the vacuum laydown zone on the forming surface into the first arcuate segment, under positive pressure into a second arcuate segment defining a pressurized take-off zone for flow through the forming surface in a direction opposite to flow of gas through the forming surface in said vacuum laydown zone, to effect removal of the laid fibrous article from the forming surface.

23. Apparatus according to claim 13, further comprising:
- arcuate walls, located in the first arcuate segment of the rotatable cylindrical drum in transverse, axially spaced relationship to one another, for dividing the first arcuate segment into transverse subsegments defining corresponding transverse vacuum laydown subzones on the forming surface; and
- flow restriction means interposed between at least one of the forming surface vacuum laydown subzones and the vacuum suction means, for effecting a transversely varying differential pressure on the forming surface vacuum laydown zone, whereby the laid fibrous article has a transversely varying basis weight.

24. Apparatus according to claim 23, wherein two arcuate walls are disposed in the first arcuate segment of the rotatable cylindrical drum to divide the first arcuate segment into three transverse subsegments defining corresponding vacuum laydown subzones on the forming surface, and wherein the flow restriction means are interposed between the transversely outer forming surface vacuum laydown subzones and the vacuum suction means.

25. Apparatus according to claim 13, further comprising means for trimming an excess thickness of a laid fibrous web deposited on the forming surface.

26. Apparatus according to claim 25, wherein the trimming means comprise a roller disposed in adjacent spaced relationship to the forming surface, and means for translating the trimming roller and forming surface in opposite directions relative to one another, to abradingly remove excess thickness of the fibrous web.

27. An apparatus as recited in claim 13, wherein said sealing flange member is arranged to extend circumferentially away from a housing which channels fibers to said forming surface.

* * * * *